(12) United States Patent
Wang et al.

(10) Patent No.: US 6,418,184 B1
(45) Date of Patent: Jul. 9, 2002

(54) HELICAL ROWWISE VIEW WEIGHTING OF COMPUTED TOMOGRAPHIC IMAGES

(75) Inventors: Sharon X. Wang, Brookfield, WI (US); Stephen W. Metz, Paris (FR); John A. Fusco, Waukesha, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/752,275

(22) Filed: Dec. 29, 2000

(51) Int. Cl.$^7$ .................................................. A61B 6/03
(52) U.S. Cl. .......................................... 378/15; 378/901
(58) Field of Search ................................ 378/4, 15, 901

(56) References Cited

U.S. PATENT DOCUMENTS

| | | |
|---|---|---|
| 5,724,037 A | 3/1998 | Lee |
| 5,825,842 A | 10/1998 | Taguchi |
| 5,828,718 A | 10/1998 | Ruth et al. |
| 5,848,117 A | 12/1998 | Urchuk et al. |
| 5,946,371 A | 8/1999 | Lai |
| 5,987,157 A | 11/1999 | Schaller et al. |
| 6,134,292 A * | 10/2000 | Hsieh .......................... 378/19 |
| 6,219,441 B1 | 4/2001 | Hu |
| 6,278,762 B1 * | 8/2001 | Hu .............................. 378/15 |
| 6,285,732 B1 | 9/2001 | Hsieh |
| 6,341,154 B1 * | 1/2002 | Besson ....................... 378/15 |

* cited by examiner

*Primary Examiner*—David V. Bruce
(74) *Attorney, Agent, or Firm*—Carl B. Horton, Esq.; Armstrong Teasdale LLP

(57) ABSTRACT

One aspect of the present invention is a method for reconstructing an image of an object utilizing a computed tomographic (CT) imaging system. The method includes steps of: helically scanning an object; interpolating an axial fan beam set of projection data as a vector function $\vec{R}_a$ from a fan beam set of projection data from the helical scan $\vec{R}_{h_i}$, where i=1, . . . , n is a row index and n represents a of number of rows of the detector array, using a relationship written as:

$$\vec{R}_a(\beta, \gamma) = \sum_{i=1}^{n} w_i(\beta)\vec{R}_{h_i}(\beta, \gamma),$$

where $w_i(\beta)$ is a weighting function written as:

$$w_i = \sum_{j=1}^{m} f(\beta - \beta_j),$$

where m is a number of images used for z smoothing, $\beta_j$ is a gantry rotation angle for a plane of reconstruction of a jth image, and $$f(x) = \begin{cases} g(x), & |x| \leq \beta_b \\ 0, & |x| > \beta_b \end{cases}$$

where constants $$\beta_b = \frac{2\pi}{p},$$

and g(x) is either a linear or non-linear function.

18 Claims, 7 Drawing Sheets

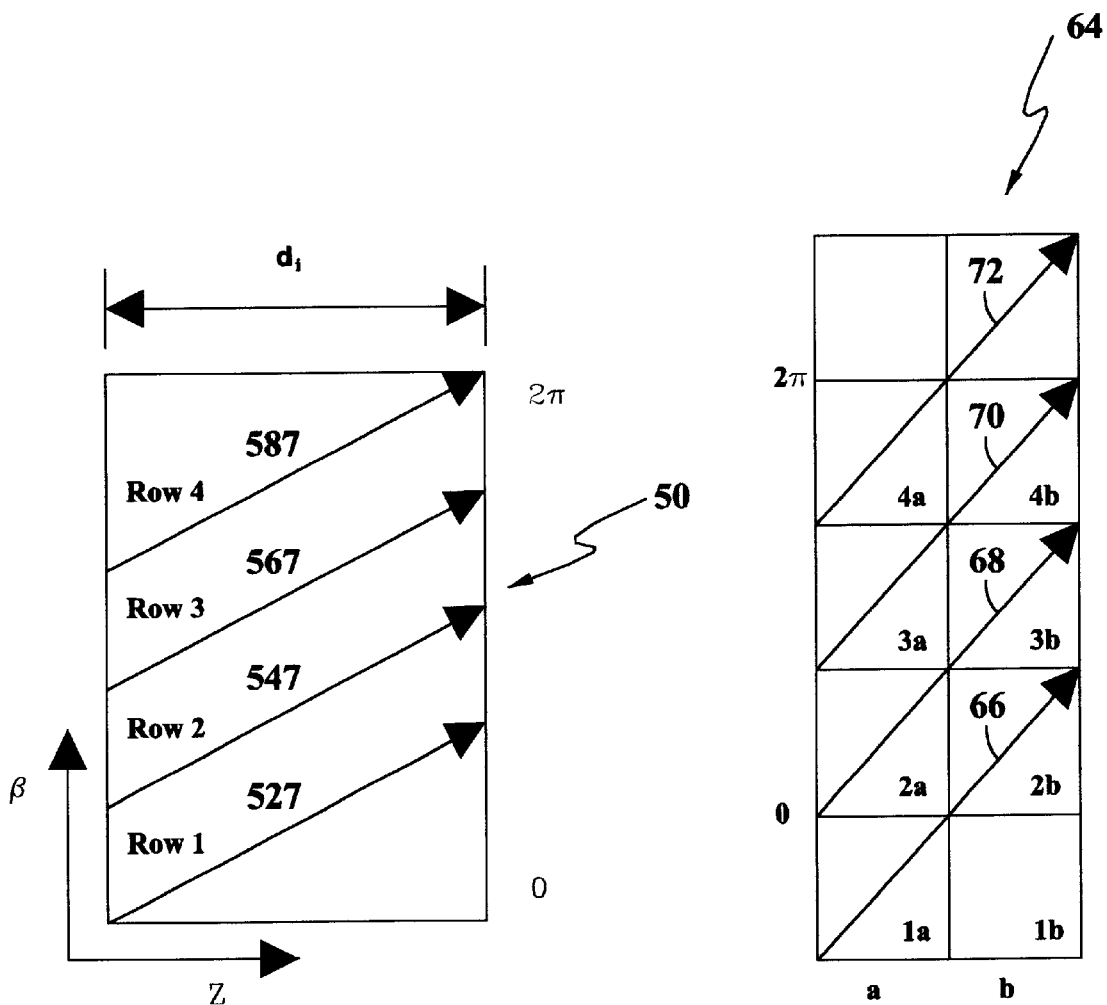
FIG. 3  FIG. 4

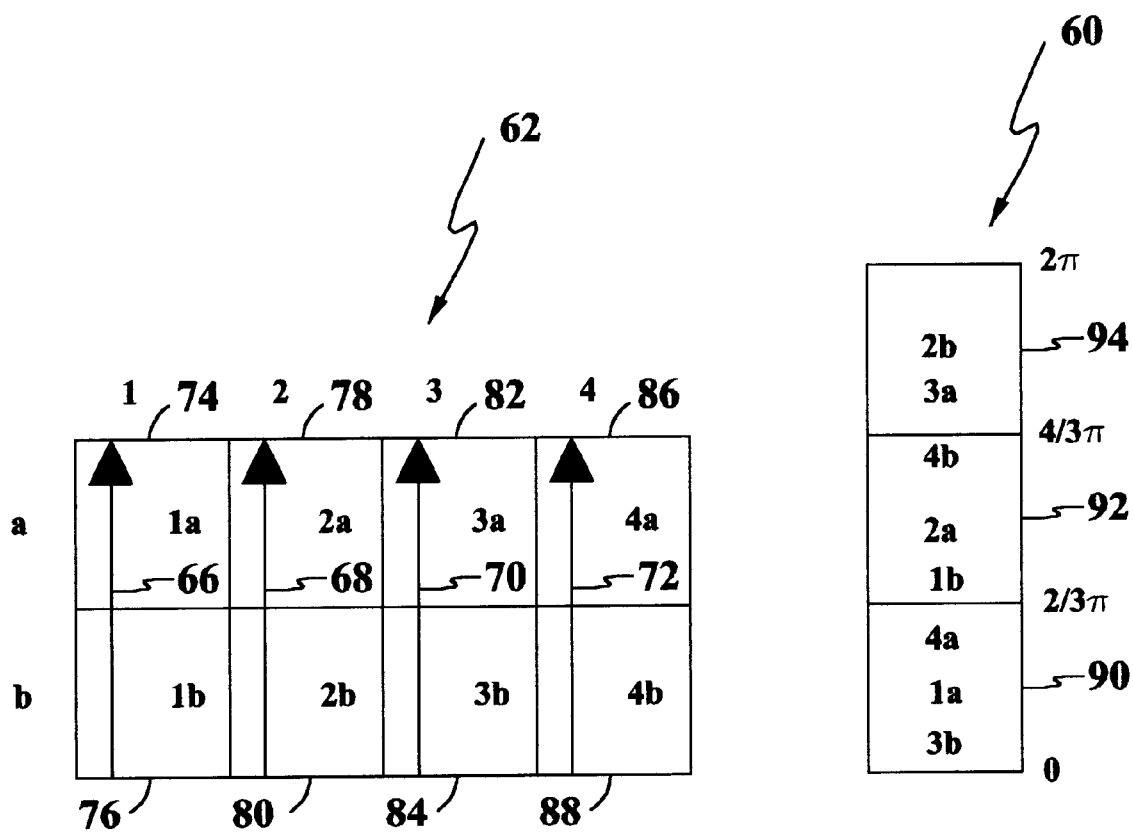
FIG. 5  FIG. 6

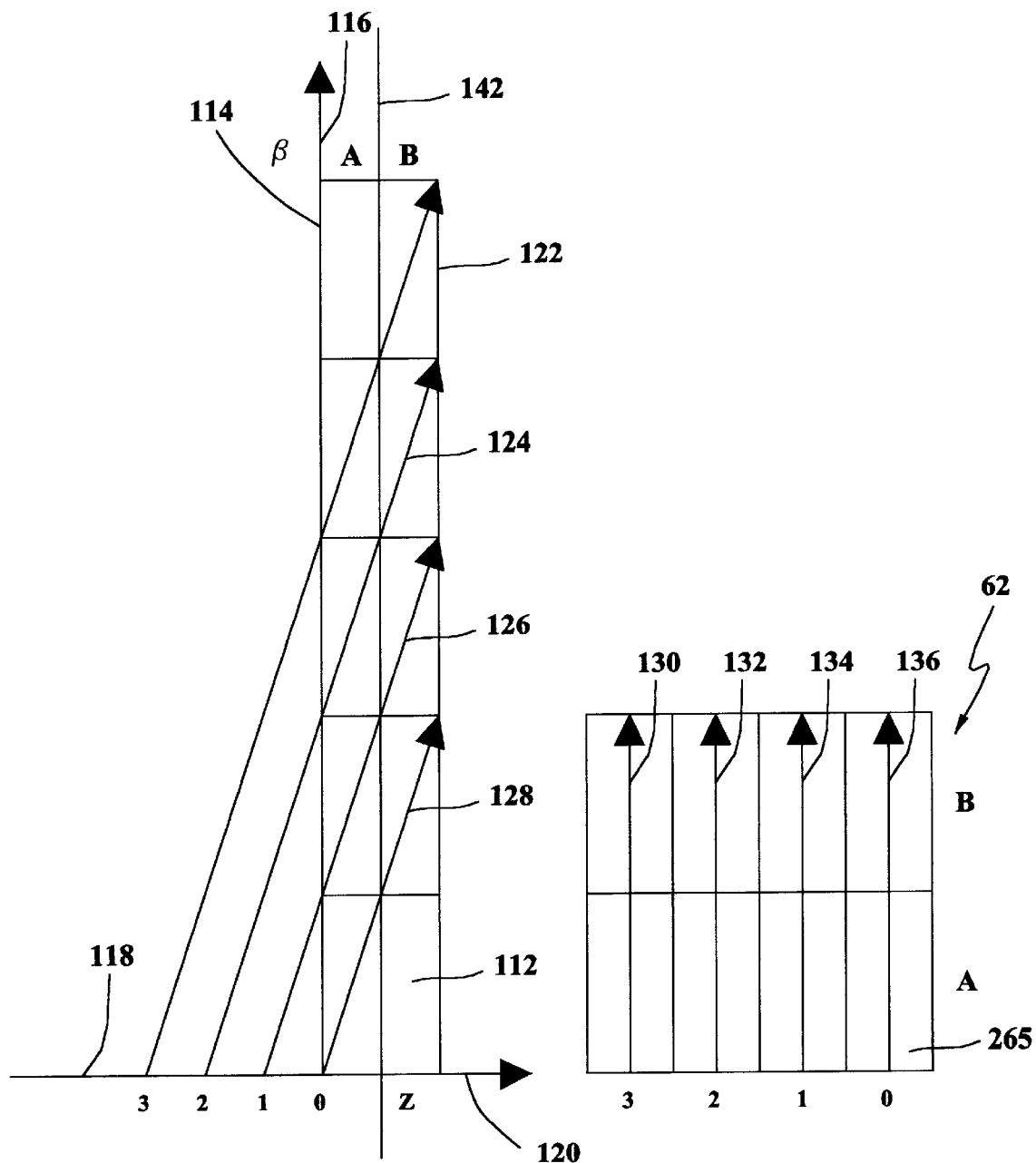
FIG. 8  FIG. 9

HELICAL ROWWISE VIEW WEIGHTING OF COMPUTED TOMOGRAPHIC IMAGES

BACKGROUND OF THE INVENTION

This invention relates generally to methods and apparatus for computed tomographic (CT) image reconstruction, and more particularly to methods for view weighting of computed tomographic image data.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

Multislice helical view weighting is a reconstruction process that generates equivalent axial scans using linear interpolation of helical scan data. Its accuracy and performance affect the overall image quality and reconstruction subsystem performance. In one known system, a z-smoothing algorithm (ZS) has been employed to provide helical view weighting. Although this known algorithm performs reasonably well in four-slice CT imaging systems, the z-smoothing algorithm is not sufficient for eight slice systems because it is too slow.

Slice sensitivity profile is a measurement that is an important indicator of image quality. The data range of the ZS algorithm is limited within $2\pi$ if overscan correction is not considered. To obtain a desirable signal to noise ratio, more data along the z-direction must be used, which results in a poor slice sensitivity profile.

Helical weighting functions play an important role in the improvement of image quality. The ZS algorithm allows limited variations of weighting functions, and therefore provides less opportunity to further improve image quality. In addition, in known high quality (HQ) Fast/premium modes, the acquired data are more than $2\pi$ within the image reconstruction range. The ZS algorithm does not fully utilize the data to further improve image quality.

The ZS algorithm also requires a large code size and thus requires a large internal memory.

It would therefore be desirable to provide methods and apparatus for fast multislice helical weighting and smoothing for CT imaging systems designed for imaging more than four slices at a time. It would also be desirable to provide methods and apparatus for helical weighting and smoothing that provides an improved slice sensitivity profile. In addition, it would be desirable to provide more variations of weighting functions and greater opportunity to improve image quality, and to fully utilize data within an image reconstruction range. Furthermore, it would be desirable to provide methods and apparatus for helical weighting and smoothing that does not require a large internal memory.

BRIEF SUMMARY OF THE INVENTION

One embodiment of the present invention is a method for reconstructing an image of an object utilizing a computed tomographic (CT) imaging system. The method includes steps of: helically scanning an object; interpolating an axial fan beam set of projection data as a vector function $\vec{R}_a$ from a fan beam set of projection data from the helical scan $\vec{R}_{h_i}$, where i=1, ..., n is a row index and n represents a of number of rows of the detector array, using a relationship written as:

$$\vec{R}_a(\beta, \gamma) = \sum_{i=1}^{n} w_i(\beta)\vec{R}_{h_i}(\beta, \gamma),$$

where $w_i(\beta)$ is a weighting function written as:

$$w_i = \sum_{j=1}^{m} f(\beta - \beta_j),$$

where m is a number of images used for z smoothing, $\beta_j$ is a gantry rotation angle for a plane of reconstrution of a jth image, and $$f(x) = \begin{cases} g(x), & |x| \leq \beta_b \\ 0, & |x| > \beta_b \end{cases}$$

where constants $$\beta_b = \frac{2\pi}{p},$$

and g(x) is either a linear or non-linear function.

Embodiments of the present invention provide a significant reduction of scan data correction post processing time. Also, embodiments of the present invention provide improved slice sensitivity profile, an ability to further reduce image artifacts and noise through the use of sophisticated weighting functions and all data available in a region, a reduction in memory usage, and a simplification of scan data correction post processing software.

BRIEF DESCRIPTION OF THE DRAWINGS

FIG. 3 is a drawing representing an image region and trajectory of a helical scan.

FIG. 4 is a representation of image space for a helical scan.

FIG. 5 is a representation of a rebin buffer of one embodiment of the present invention.

FIG. 6 is a representation of a projection buffer of one embodiment of the present invention.

FIG. 8 is a schematic representation of a region in which an image is to be reconstructed, showing a plane of reconstruction.

FIG. 9 is a representation of results of rebinning, showing representations of selected and stored scan data.

DETAILED DESCRIPTION OF THE INVENTION

Figure 1:
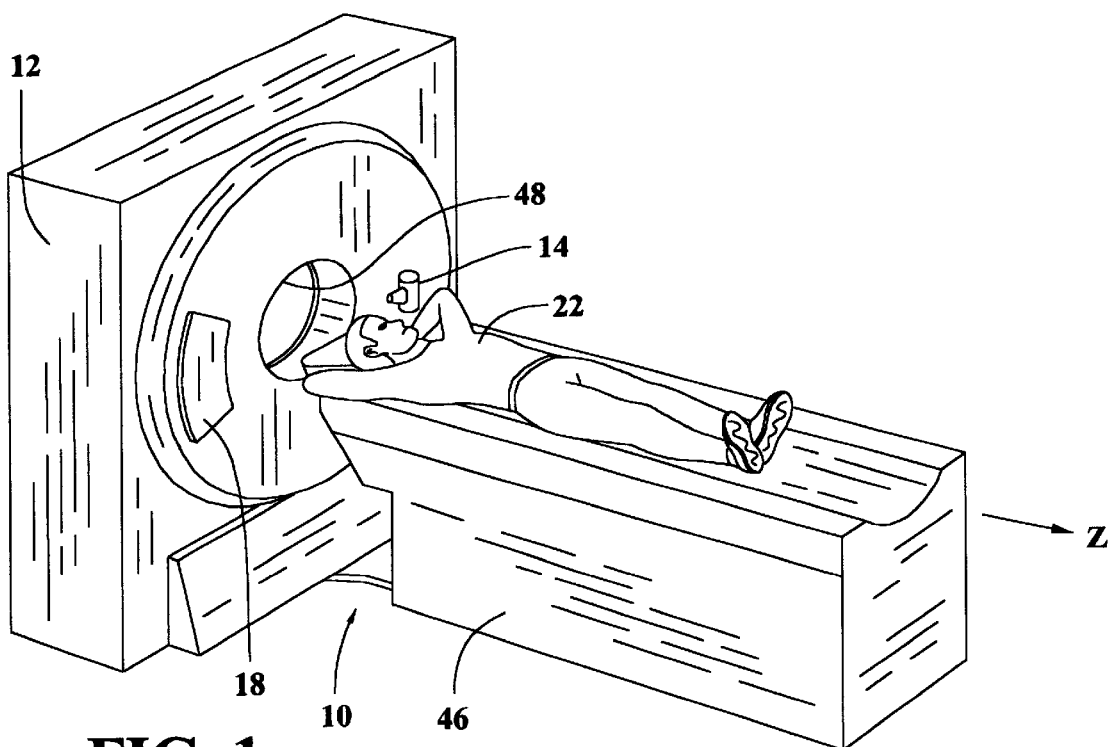
FIG. 1 is a pictorial view of a CT imaging system embodiment.
Figure 2:
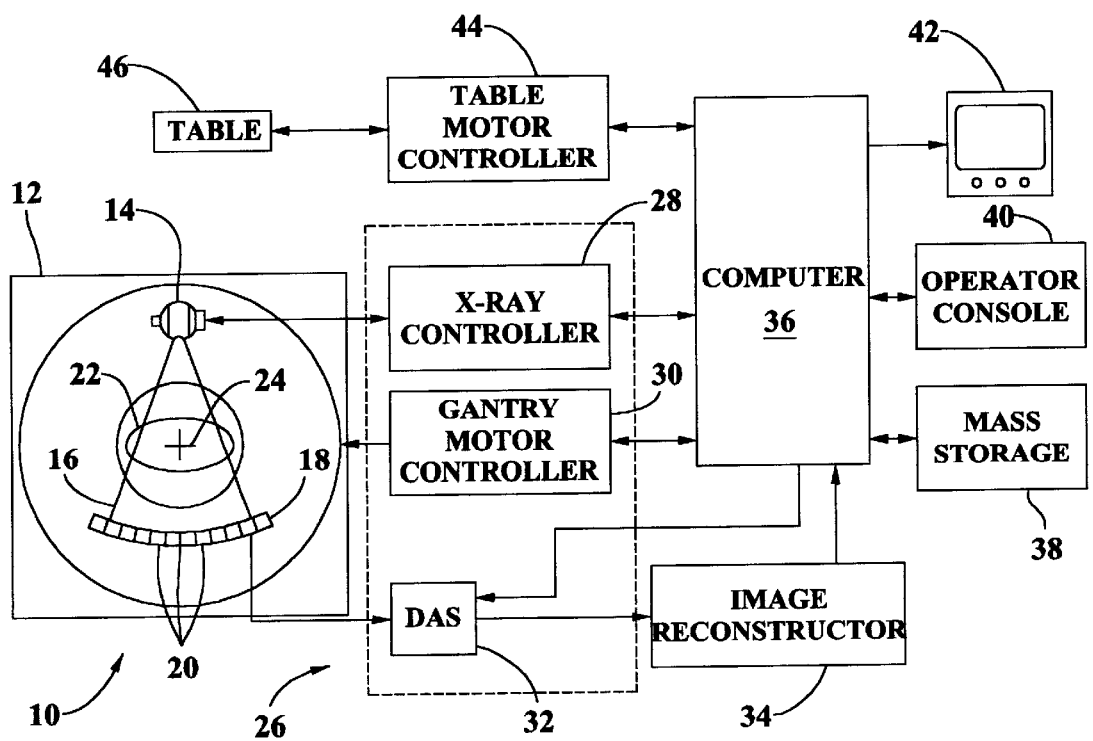
FIG. 2 is a block schematic diagram of the system illustrated in FIG. 1.

In one embodiment and referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24. Detector array 18 may be fabricated in a single slice or multi-slice configuration. In a multi-slice configuration, detector array 18 has a plurality of rows of detector elements 20, only one of which is shown in FIG. 2.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In a multislice imaging system 10, detector array 18 comprises a plurality of parallel detector rows, wherein each row comprises a plurality of individual detector elements 20. An imaging system 10 having a multislice detector 18 is capable of providing a plurality of images representative of a volume of object 22. Each image of the plurality of images corresponds to a separate "slice" of the volume. The "thickness" or aperture of the slice is dependent upon the thickness of the detector rows.

One embodiment of the present invention utilizes a row-wise (RW) interpolation algorithm for helical scan weighting. RW view weighting is based on a trajectory of detector 18 during a helical scan, and is both simple and highly efficient.

Denote a fan beam from an axial scan as a vector function $\vec{R}_a$ and a fan beam from a helical scan as $\vec{R}_{h_i}$, where i=1, . . . , n is the row index and n represents the of number of detector rows. The RW interpolation is written as $$\vec{R}_a(\beta, \gamma) = \sum_{i=1}^{n} w_i(\beta) \vec{R}_{h_1}(\beta, \gamma), \quad (1)$$

where $w_i(\beta)$ is the weighting function. In one embodiment, $w_i(\beta)$ is written:

$$w_i = \sum_{j=1}^{m} f(\beta - \beta_j). \quad (2)$$

In Equation (2), m is the number of image used for z smoothing. $\beta_j$ is the gantry rotation angle for the plane of reconstrution of $j_{th}$ image. The base weighting function f is written:

$$f(x) = \begin{cases} g(x), & |x| \le \beta_b \\ 0, & |x| > \beta_b \end{cases}$$

where constants $$\beta_b = \frac{2\pi}{p},$$

and g(x) is linear function in one embodiment, and a nonlinear function in another embodiment. P is the helical pitch.

In one embodiment, rowwise interpolation is used to generate an axial fan beam set, and n×m multiplications and (n−1)×m additions are used, where m is the number of detector elements 20.

A region where helical data is fetched for image reconstruction is important for image quality and software structure. In one embodiment of the present invention and referring to FIG. 3, the RW algorithm uses data from image space 50, where arrows 52, 54, 56, and 58 represent a trajectory of a first, second, third, and fourth row of helical data. The coordinate system (z,β) is set so that the z-axis indicates table 46 motion direction z and the β-axis indicates gantry 12 rotation angle β.

In one embodiment of the present invention, RW uses as input a ratio written as:

$$r_a = d_i/d_r, \quad (4)$$

where $d_i$ is the width of image space 50 and $d_r$ is the row thickness. Once $r_a$ is determined, all views having trajectories 52, 54, 56, and 58 that pass an image space defined by $r_a$ are used for helical row weighting. In this manner, the number of super views used often exceeds $2\pi$, which is desirable because the fact that the number of views is fixed implies that as the angle $\beta$ increases, the spatial resolution improves.

The reconstruction region of RW in one embodiment of the present invention has the following characteristics: First, the data region for the RW algorithm is smaller in the z direction for a given number of views, which results in a thinner slice sensitivity profile. Second, the data region for the RW algorithm has the same number of views for all rows, which reduces the image skew inherited from helical scanning. The result is a rectangular rebin buffer that simplifies the software architecture and improves performance significantly.

Given a helical pitch p and a ratio $r_a$, the number of views used for reconstruction in one embodiment is written:

$$v = \frac{T}{p}(r + r_a - 1), \quad (5)$$

where T is detector sampling rate per rotation, and r is the number of detector rows.

In one embodiment of the present invention, a loop that performs vector multiplication and addition is used to accomplish weighting as described by equation (1). In another embodiment and referring to FIGS. 4, 5, and 6, to improve performance, views first written to a projection buffer 60 are separated from views that are added to the views that already reside in projection buffer 60. This optimization allows the buffer initialization and a condition test to be eliminated.

The rectangular shape of rebin buffer 62 results in a very simple control loop. Dividing a row of views into $r_a$ sections, the first sections of all rows except the last row are the first data written into the projection buffer and the rest are added to them. If $r_a$ is not an integer, then the ceiling of $r_a$ is used. Data is transferred from prep buffer 64 into projection buffer 60 when $r_a=2$, for a four slice scanner. A similar control flow can be used for any number of slices. Arrows 66, 68, 70, and 72 represent four rows of prepared data from image space 50. The prepared data is divided into two sections a and b, each of which has a width equal to the row width. Rebin buffer 62 is structured into areas 74, 76, 78, 80, 82, 84, 86, and 88. Arrows 66, 68, 70, and 72 represent prepared data transferred from the corresponding image space. Indices in areas 74, 76, 78, 80, 82, 84, 86, and 88 indicate data transferred from a corresponding location in image space 50. The indices represent the data transferred from the corresponding location in the image space. Projection buffer 60 is divided into areas 90, 92, and 94. Indices in areas 90, 92, and 94 indicate which portion of the prepared data has been deposited in the corresponding buffer 60 portion 90, 92, or 94. Rows 1 and 4 (corresponding to arrows 66, 68, 70, and 72) occupy the same buffer 60 space when helical pitch 3 is used, because both rows are overlapped and treated as the same data.

Embodiments of the present invention achieve a processing time as low as 0.12 seconds with known DSP hardware. In addition, image quality as measured by slice sensitivity profile (SSP) is high in terms of full width half maximum (FWHM). In addition, the shape of the SSP is closer to trapezoidal, as is the SSP of an axial scan.

Figure 7:
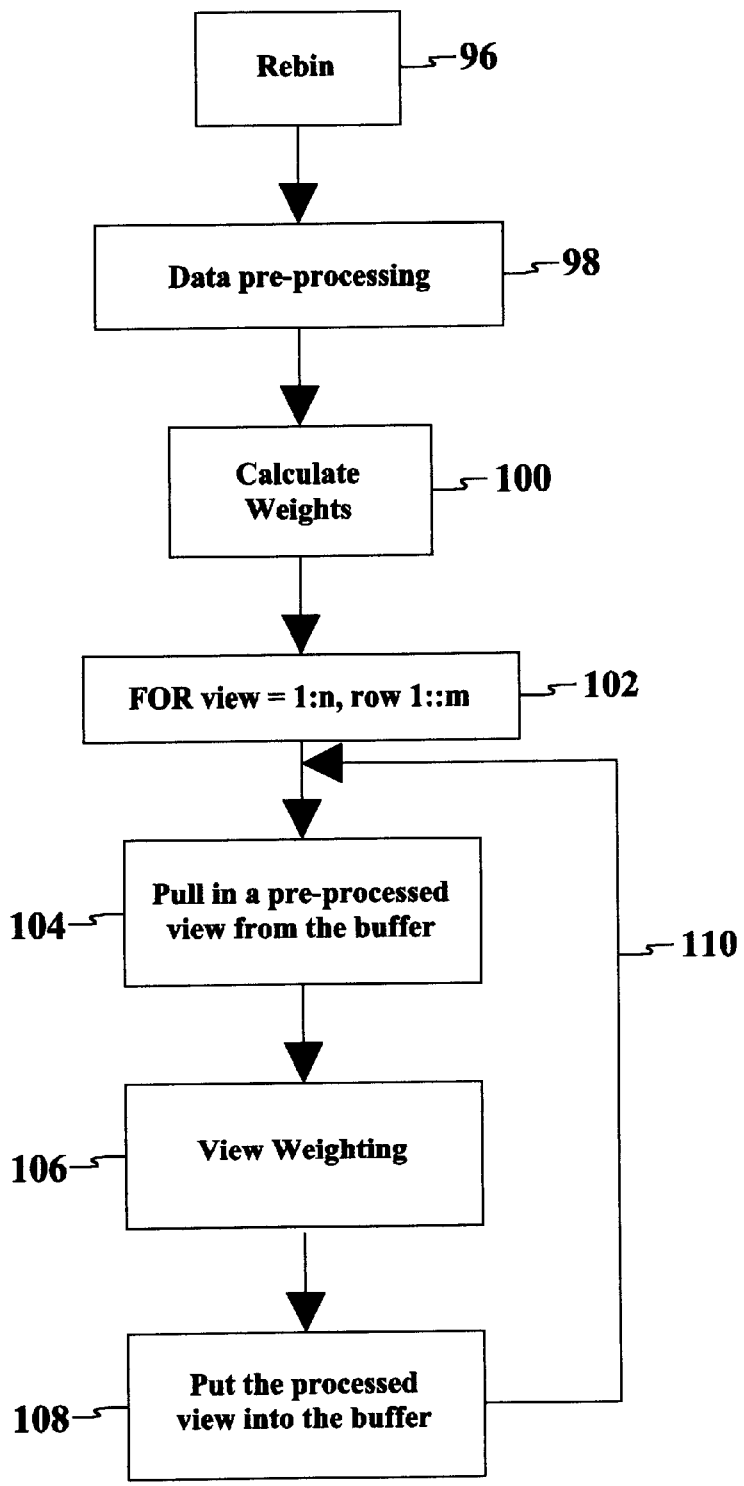
FIG. 7 is a flow chart of a helical weighting procedure embodiment of the present invention.

In one embodiment and referring to FIG. 7, data is rebinned 96, i.e., aligned and stored for efficient processing and view weighting. After rebinning, the data is preprocessed 98 to prepare scan data for view weighting and image generation. Weights are then calculated 100, and a processing loop 102 for the data is begun. A preprocessed view is obtained 104 from a RAM buffer, and the preprocessed view is weighted 106, including multiplication and summation as necessary. The weighted projection data is them output 108 to the buffer. Repetitions 110 of the process 104, 106, and 108 are performed for all input views and rows required to make an image. The weighted data is used to reconstruct an image of the object.

In one embodiment and referring to FIG. 8, an image is reconstructed in a region 112, delimited by a left boundary 114. Arrow 116 indicates a direction of gantry rotation as measured by angle $\beta$, which is measured from starting point 118. Table 46 moves in a z-direction 120, the movement of which is measured in millimeters. Region 112 is divided into subregions in both the $\beta$ and z-direction. The number of subregions in the z-direction is determined by the thickness of an image slice and the detector aperture. In one embodiment, two subregions A and B are used, and imaging system 10 utilizes a detector array 18 having four rows of detector elements 20. Detector data is acquired over scanning paths 112, 124, 126, and 128.

In one embodiment and referring to FIG. 9, a rebin buffer 62 is provided that is divided into rows and subregions A and B, corresponding to the rows of detector array 18 and subregions A and B of FIG. 8. The results of the rebinning are selected and stored scan data 130, 132, 134, 136, which correspond to scan data 122, 124, 126, and 128.

Figure 10:
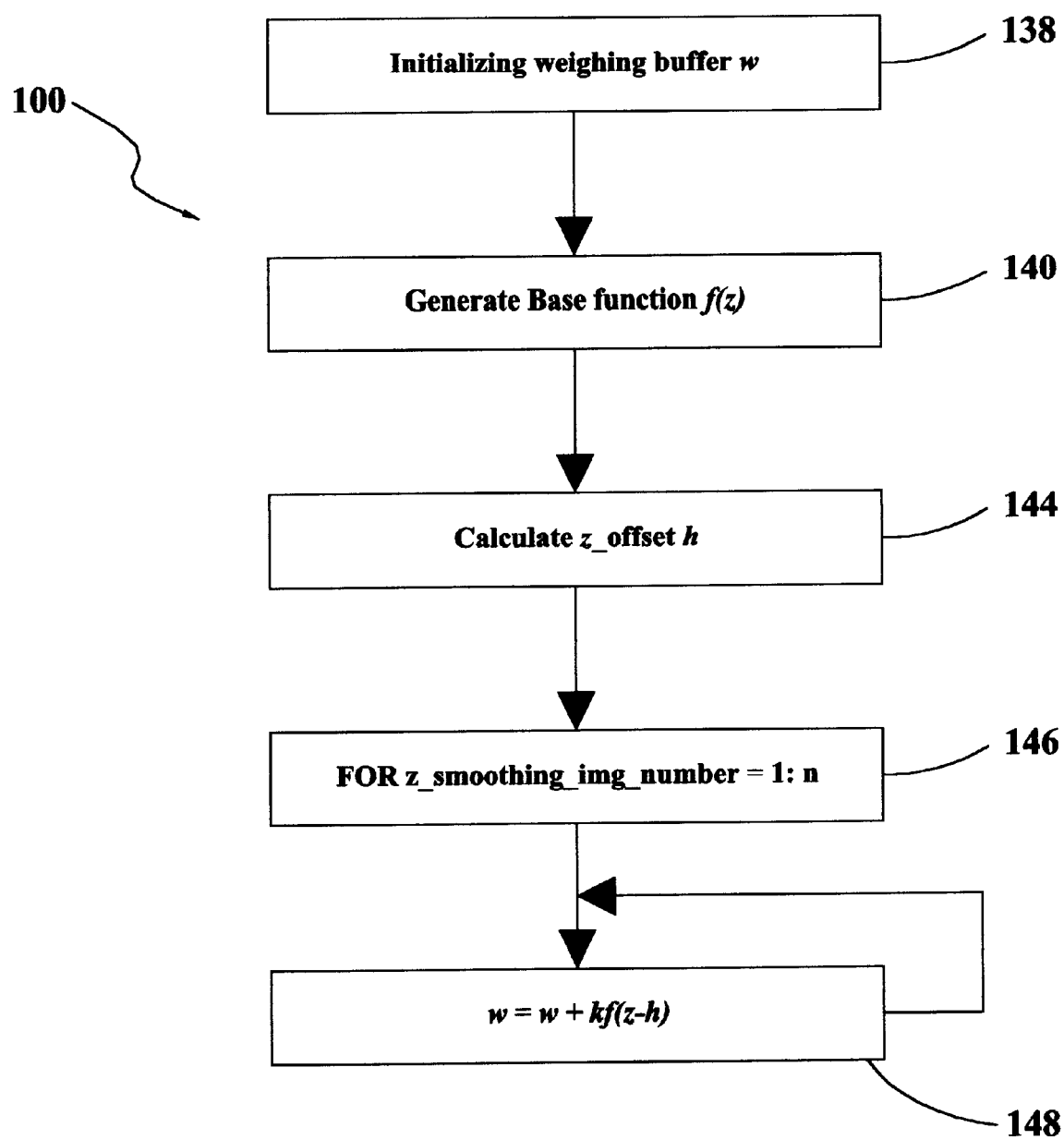
FIG. 10 is a flow chart showing details weighting function generation of the helical weighting procedure embodiment of FIG. 7.

In one embodiment and referring to FIG. 10, weighting function generation 100 is performed by initialing 138 a weighting buffer w to a zero value. Next, a base weighting function f(z) is generated 140, where z is a distance from the scan data location to a plane of reconstruction 142 (shown in FIG. 8). Next, an offset is calculated 144 for z-smoothing images. A loop 146, 148 is used to sum all weights with offset h. The value k in 148 is a weight for each z-smoothing image.

Figure 11:
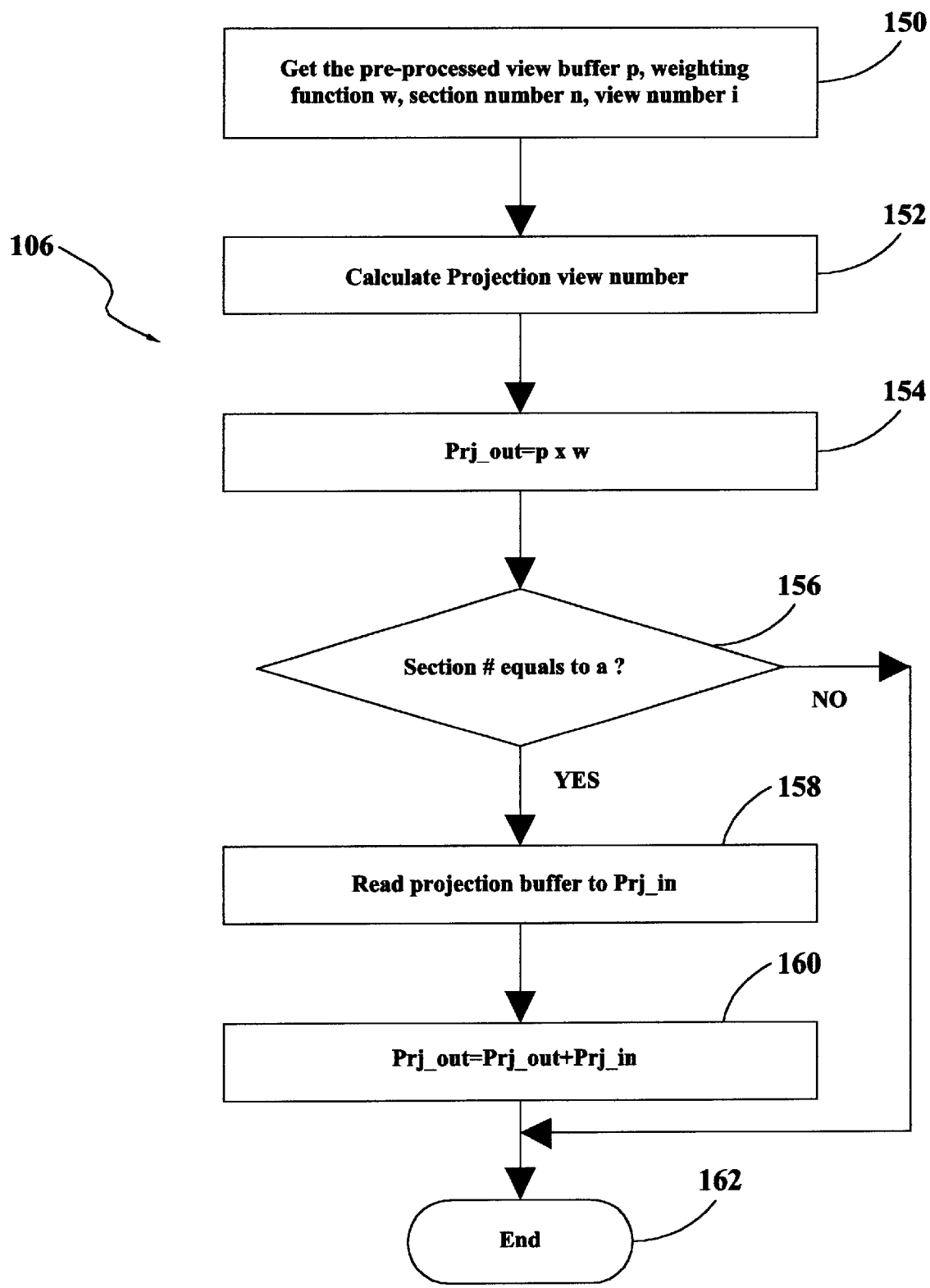
FIG. 11 is a flow chart showing details of the view weighting function of the helical weighting procedure embodiment of FIG. 7.

In one embodiment and referring to FIG. 11, view weighting 106 comprises obtaining parameters 150 for the view weighting function, including the pre-processed view buffer p, weighting function w, section number n, and view number i. A projection view number is calculated 152 to determine where to store the result. Weights are then multiplied 154 as written by Prj_out=p×w. If a comparison 156 indicates that the section being weighted is section A, then the projection buffer is read 158 into Prj_in, and Prj_out is set 160. Otherwise, the function exits 162.

In one embodiment of the present invention, the steps of the helical rowwise view weighting procedure are performed within imaging system 10. For example, a software or firmware program executed by image reconstructor 34 hardware performs the helical rowwise view weighting. In another embodiment of the present invention, another processor (not shown) not part of imaging system is used to perform image reconstruction functions from acquired data, including the functions of helical rowwise view weighting.

It would therefore be desirable to provide methods and apparatus for fast multislice helical weighting and smoothing for CT imaging systems designed for imaging more than four slices at a time. It would also be desirable to provide methods and apparatus for helical weighting and smoothing that provides an improved slice sensitivity profile. In addition, it would be desirable to provide more variations of weighting functions and greater opportunity to improve image quality, and to fully utilize data within an image reconstruction range. Furthermore, it would be desirable to provide methods and apparatus for helical weighting and smoothing that does not require a large internal memory.

While the invention has been described in terms of various specific embodiments, those skilled in the art will recognize that the invention can be practiced with modification within the spirit and scope of the claims.

What is claimed is:

1. A method for reconstructing an image of an object utilizing a computed tomographic (CT) imaging system having a radiation source and a multislice detector array on a rotating gantry, the radiation source configured to project a beam of radiation through an object and towards the multislice detector array, the multislice detector array configured to sense attenuation of the radiation passing through the object;

said method comprising the steps of:

helically scanning an object with a computed tomographic imaging system to acquire a plurality of slices of projection data;

interpolating an axial fan beam set of projection data as a vector function $\vec{R}_a$ from a fan beam set of projection data from the helical scan $\vec{R}_{h_i}$, where i=1, . . . , n is a row index and n represents a of number of rows of the detector array, using a relationship written as:

$$\vec{R}_a(\beta, \gamma) = \sum_{i=1}^{n} w_i(\beta) \vec{R}_{h_i}(\beta, \gamma),$$

where $w_i(\beta)$ is a weighting function written as:

$$w_i = \sum_{j=1}^{m} f(\beta - \beta_j),$$

where m is a number of images used for z smoothing, $\beta_j$ is a gantry rotation angle for a plane of reconstrution of a jth image, and $$f(x) = \begin{cases} g(x), & |x| \leq \beta_b \\ 0, & |x| > \beta_b \end{cases}$$

where constants $$\beta_b = \frac{2\pi}{p},$$

and g(x) is either a linear or non-linear function.

2. A method in accordance with claim 1 wherein g(x) is a linear function.

3. A method in accordance with claim 1 wherein g(x) is a nonlinear function.

4. A method in accordance with claim 1 wherein all views passing an image space defined by $r_a = d_i/d_r$ are used for helical row weighting, where $d_i$ is a width of an image space and $d_r$ is a row thickness.

5. A method in accordance with claim 4 wherein a number of super views exceeds $2\pi$.

6. A method in accordance with claim 4 wherein said step of helically scanning comprises helically scanning at a helical pitch of p, and wherein a number of views v used for reconstruction is written:

$$v = \frac{T}{p}(r + r_a - 1),$$

where T is a detector sampling rate per rotation, and r is the number of detector rows.

7. A method for reconstructing an image of an object utilizing a computed tomographic (CT) imaging system having a radiation source and a multislice detector array on a rotating gantry, the radiation source configured to project a beam of radiation through an object and towards the multislice detector array, the multislice detector array configured to sense attenuation of the radiation passing through the object;

said method comprising the steps of:

helically scanning an object with a computed tomographic imaging system to acquire a plurality of slices of projection data;

rebinning the projection data to align and store helical scan data for view weighting;

generating a view weighting function;

looping, for each view and for each row of the multislice detector array, to retrieve and to view weight the helical scan data, and to write the weighted data to a buffer; and reconstructing an image of the object using the weighted data.

8. A method in accordance with claim 7 wherein said step of generating a view weighting function comprises the steps of:

initializing a buffer for storing the weighting function;

generating a base weighting function f(z), where z is a distance from a scan data location to a plane of reconstruction;

calculating an offset for z-smoothing images; and summing all weights with an offset h.

9. A method in accordance with claim 8 wherein view weighting the helical scan data comprises the steps of:

obtaining parameters for a view weighting function;

calculating a projection view number to determine a location to store the weighted data in the buffer; and multiplying the helical scan data by the view weighting function.

10. A computed tomographic (CT) imaging system for reconstructing an image of an object, said computed tomographic (CT) imaging system comprising a radiation source and a multislice detector array on a rotating gantry, said radiation source configured to project a beam of radiation through an object and towards said multislice detector array, said multislice detector array configured to sense attenuation of said radiation beam passing through the object;

said imaging system configured to:

helically scan an object to acquire a plurality of slices of projection data;

interpolate an axial fan beam set of projection data as a vector flnction $\vec{R}_a$ from a fan beam set of projection data from the helical scan $\vec{R}_{h_i}$, where i=1, . . . , n is a row index and n represents a of number of rows of the detector array, using a relationship written as:

$$\vec{R}_a(\beta, \gamma) = \sum_{i=1}^{n} w_i(\beta) \vec{R}_{h_i}(\beta, \gamma),$$

where $w_i(\beta)$ is a weighting function written as:

$$w_i = \sum_{j=1}^{m} f(\beta - \beta_j),$$

where m is a number of images used for z smoothing, $\beta_j$ is a gantry rotation angle for a plane of reconstrution of a jth image, and $$f(x) = \begin{cases} g(x), & |x| \leq \beta_b \\ 0, & |x| > \beta_b \end{cases}$$

where constants $$\beta_b = \frac{2\pi}{p},$$

and g(x) is either a linear or non-linear function.

11. An imaging system in accordance with claim 10 wherein g(x) is a linear function.

12. An imaging system in accordance with claim 10 wherein g(x) is a nonlinear function.

13. An imaging system in accordance with claim 10 configured to use all views passing an image space defined by $r_a = d_i/d_r$ for helical row weighting, where $d_i$ is a width of an image space and $d_r$ is a row thickness.

14. An imaging system in accordance with claim 13 configured to utilize a number of super views exceeding $2\pi$.

15. An imaging system in accordance with claim 13 wherein to helical scan the object, said imaging system is configured to helically scan at a helical pitch of p, and said imaging system is configured to utilize a number of views v for reconstruction, where v is written:

$$v = \frac{T}{p}(r + r_a - 1),$$

where T is a detector sampling rate per rotation, and r is the number of detector rows.

16. A computed tomographic (CT) imaging system for reconstructing an image of an object, said computed tomographic (CT) imaging system comprises a radiation source and a multislice detector array on a rotating gantry, said radiation source configured to project a beam of radiation through an object and towards said multislice detector array, said multislice detector array configured to sense attenuation of said radiation passing through the object;
said imaging system configured to:
helically scan an object with a computed tomographic imaging system to acquire a plurality of slices of projection data;
rebin the projection data to align and store helical scan data for view weighting;
generate a view weighting function;
loop, for each view and for each row of the multislice detector array, to retrieve and to view weight the helical scan data, and to write the weighted data to a buffer; and
reconstruct an image of the object using the weighted data.

17. An imaging system in accordance with claim 16 wherein to generate a view weighting function, said imaging system is configured to:
initialize a buffer for storing the weighting function;
generate a base weighting function f(z), where z is a distance from a scan data location to a plane of reconstruction;
calculate an offset for z-smoothing images; and
sum all weights with an offset h.

18. An imaging system in accordance with claim 17 wherein to view weight the helical scan data, said imaging system is configured to:
obtain parameters for a view weighting function;
calculate a projection view number to determine a location to store the weighted data in the buffer; and
multiply the helical scan data by the view weighting function.

* * * * *

UNITED STATES PATENT AND TRADEMARK OFFICE
CERTIFICATE OF CORRECTION

PATENT NO. : 6,418,184 B1
DATED : July 9, 2002
INVENTOR(S) : Sharon X. Wang et al.

It is certified that error appears in the above-identified patent and that said Letters Patent is hereby corrected as shown below:

<u>Column 8,</u>
Line 63, delete "flnction" insert therefor -- function --.

Signed and Sealed this

Eleventh Day of November, 2003

JAMES E. ROGAN
*Director of the United States Patent and Trademark Office*